(12) United States Patent
Sandhu et al.

(10) Patent No.: US 11,833,042 B2
(45) Date of Patent: Dec. 5, 2023

(54) DEVICE AND METHODS FOR SELF-CENTERING A GUIDE CATHETER

(71) Applicant: Mayo Foundation for Medical Education and Research, Rochester, MN (US)

(72) Inventors: Gurpreet S. Sandhu, Rochester, MN (US); Daniel B. Spoon, Rochester, MN (US); Brandon J. Tefft, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 765 days.

(21) Appl. No.: 16/806,790

(22) Filed: Mar. 2, 2020

(65) Prior Publication Data
US 2020/0237511 A1 Jul. 30, 2020

Related U.S. Application Data

(63) Continuation of application No. 15/872,510, filed on Jan. 16, 2018, now Pat. No. 10,709,558, which is a continuation of application No. 14/906,393, filed as application No. PCT/US2014/047541 on Jul. 22, 2014, now Pat. No. 9,889,006.
(Continued)

(51) Int. Cl.
*A61F 2/24* (2006.01)
*A61M 25/01* (2006.01)
*A61M 25/04* (2006.01)
*A61M 25/09* (2006.01)

(52) U.S. Cl.
CPC ....... *A61F 2/2427* (2013.01); *A61M 25/0108* (2013.01); *A61M 25/04* (2013.01); *A61M 25/09* (2013.01)

(58) Field of Classification Search
None
See application file for complete search history.

(56) References Cited

U.S. PATENT DOCUMENTS

| 5,011,488 A | 4/1991 | Ginsburg |
| 6,171,328 B1 | 1/2001 | Addis |

(Continued)

FOREIGN PATENT DOCUMENTS

| CN | 1278711 A | 1/2001 |
| CN | 101553190 A | 10/2009 |

(Continued)

OTHER PUBLICATIONS

European Search Report for European Application No. 14829758.3, dated Feb. 22, 2017, 4 pages.
(Continued)

*Primary Examiner* — Manuel A Mendez
(74) *Attorney, Agent, or Firm* — Seager, Tufte & Wickhem, LLP (57) ABSTRACT

This document provides devices and methods for the treatment of heart conditions such as valvular stenosis. For example, this document provides devices and methods by which a guide catheter can align itself with a blood flow stream to thereby help direct a guidewire or other elongate device transmitted from the guide catheter through an orifice of a heart valve.

19 Claims, 5 Drawing Sheets

Related U.S. Application Data (60) Provisional application No. 61/856,910, filed on Jul. 22, 2013.

(56) References Cited

U.S. PATENT DOCUMENTS

| | | |
|---|---|---|
| 7,232,462 B2 | 6/2007 | Schaeffer |
| 8,133,213 B2 | 3/2012 | Lashinski |
| 8,372,133 B2 | 2/2013 | Douk et al. |
| 8,845,583 B2 | 9/2014 | Boyle et al. |
| 9,889,006 B2 | 2/2018 | Sandhu et al. |
| 10,709,558 B2 | 4/2020 | Sandhu et al. |
| 2002/0143361 A1 | 10/2002 | Douk et al. |
| 2004/0082910 A1 | 4/2004 | Constantz et al. |
| 2005/0096734 A1 | 5/2005 | Majercak et al. |
| 2005/0124969 A1 | 6/2005 | Fitzgerald et al. |
| 2005/0222604 A1 | 10/2005 | Schaeffer |
| 2006/0020327 A1 | 1/2006 | Lashinski et al. |
| 2006/0259136 A1 | 11/2006 | Nguyen et al. |
| 2006/0293647 A1* | 12/2006 | McRae ............ A61M 25/0068 604/93.01 |
| 2008/0097402 A1 | 4/2008 | Hoganson et al. |
| 2010/0168844 A1 | 7/2010 | Toomes et al. |
| 2011/0082464 A1 | 4/2011 | Douk et al. |
| 2011/0288578 A1 | 11/2011 | Angel |
| 2012/0053680 A1 | 3/2012 | Bolling et al. |
| 2012/0059309 A1 | 3/2012 | Di Palma et al. |
| 2012/0116351 A1 | 5/2012 | Chomas et al. |
| 2013/0102926 A1 | 4/2013 | Eliason et al. |

FOREIGN PATENT DOCUMENTS

| | | |
|---|---|---|
| JP | 2002336261 A | 11/2002 |
| JP | 2007509701 A | 4/2007 |
| JP | 2007125409 A | 5/2007 |
| JP | 2008539985 A | 11/2008 |
| WO | 199912489 A2 | 3/1999 |
| WO | 2007035471 A2 | 3/2007 |
| WO | 2010119445 A1 | 10/2010 |
| WO | 2011085266 A2 | 7/2011 |
| WO | 2013037505 A1 | 3/2013 |
| WO | 2013166049 A1 | 11/2013 |

OTHER PUBLICATIONS

European Office Action for European Application No. 14829758.3, dated Mar. 22, 2017, 5 pages.

Invitation to Pay for PCT/US2014047541, dated Nov. 18, 2014, 2 pages.

International Search Report and Written Opinion for PCT/US2014/047541, dated Feb. 10, 2015, 17 pages.

International Preliminary Report on Patentability for PCT/US2014/047541, dated Feb. 4, 2016, 8 pages.

Chinese Office Action in International Application No. CN201480041420.2, dated Jun. 4, 2018, 13 pages (with English translation).

Japanese Office Action in International Application No. JP2016-529823, dated Mar. 28, 2018, 8 pages (with English translation).

* cited by examiner

DEVICE AND METHODS FOR SELF-CENTERING A GUIDE CATHETER

CROSS-REFERENCE TO RELATED APPLICATIONS

This application is a continuation of U.S. patent application Ser. No. 15/872,510, filed Jan. 16, 2018, which is a continuation of U.S. patent application Ser. No. 14/906,393, filed Jan. 20, 2016 (now U.S. Pat. No. 9,889,006), which is a National Stage application under 35 U.S.C. § 371 of International Application No. PCT/US2014/047541, filed Jul. 22, 2014, which claims the benefit of U.S. Provisional Application Ser. No. 61/856,910, filed Jul. 22, 2013. The disclosures of the prior applications are considered part of (and are incorporated by reference in) the disclosure of this application.

BACKGROUND

1. Technical Field

This document relates to devices and methods for the treatment of heart conditions such as valvular stenosis. For example, this document relates to devices and methods by which a guide catheter can align itself with a blood flow stream to thereby help direct a guidewire or other elongate device transmitted from the guide catheter through an orifice of a heart valve, or any other normal or abnormal passage in the body against the direction flow. This device can also be used to localize and repair leaks where a fluid flow jet is present in submerged or fluid-filled chambers.

2. Background Information

Cardiac valvular stenosis is a condition in which the heart's valves are narrowed (stenotic). With valvular stenosis, the tissues forming the valve leaflets become stiffer, narrowing the valve opening, and reducing the amount of blood that can flow through it. If the stenosis is mild, the overall cardiac output remains normal. However, when the valves can become severely stenotic, that can lead to a reduction in cardiac output and impairment of heart function.

Mitral valve stenosis is an abnormal narrowing of the mitral valve, resulting in a restriction of the blood flow from the left atrium to the left ventricle. The atrium heart chamber may enlarge as pressure builds up. Blood and fluid may then collect in the lung tissue (pulmonary edema), making it hard to breathe. Mitral valve stenosis can make a person severely short of breath, among other problems.

Aortic valve stenosis occurs when the heart's aortic valve narrows. When the aortic valve is so obstructed, the heart has to work harder to pump blood to the body. Eventually, this extra work limits the amount of blood the heart can pump, and may weaken the heart muscle. The left atrium may enlarge as pressure builds up, and blood and fluid may then collect in the lung tissue (pulmonary edema), making it hard to breathe. Medications can ease symptoms of mild to moderate aortic valve stenosis. However, the only way to treat severe aortic valve stenosis is by surgery to replace the valve.

Therapies to repair or replace the aortic valve include balloon valvuloplasty (valvotomy), surgical aortic valve replacement, and transcatheter aortic valve replacement (TAVR). TAVR involves replacing the aortic valve with a prosthetic valve that is delivered via the femoral artery (transfemoral) or the left ventricular apex of the heart (transapical). TAVR is sometimes referred to as transcatheter aortic valve implantation (TAVI).

One of the most challenging steps when performing a TAVR, valvuloplasty, or hemodynamic study on a stenotic aortic valve is to find the valve orifice and pass a guidewire, catheter, or other elongate medical device through this severely stenotic valve. The current practice involves random probing of the stenotic valve with the guide wire until the orifice is penetrated. The high-pressure jet of blood coming out of the narrowed valve makes it even more challenging to align a catheter and advance against the direction of flow. Prolonged probing increases the risk or dislodging small amounts of calcified debris and atheroma from the valve surface and can lead to strokes.

SUMMARY

This document provides devices and methods for the treatment of heart conditions such as valvular stenosis. For example, this document provides devices and methods by which a guide catheter can align itself with a blood flow stream to thereby help direct a guidewire or other elongate device transmitted from the guide catheter through an orifice of a heart valve, against the direction of flow.

The devices and methods provided herein may save time and expense during cardiac catheterization procedures by quickly aligning the guide catheter with the valve orifice such that a guidewire transmitted from the guide catheter can pass through the stenotic valve orifice without the need for random probing. This can reduce the risk of thromboembolic strokes, and reduce radiation exposure for patients and physicians. The devices and methods can be used for TAVR procedures as well as for diagnostic investigations where there is a need to cross the aortic valve to measure a pressure gradient in aortic stenosis cases. In addition to treating aortic stenosis, the devices and methods provided herein have applications for perivalvular mitral valve leaks and any other fistulas where there is a need to find a fluid flow and to cross against the fluid flow. Non-medical applications may include directing closure devices across holes or channels in equipment such as ships/boats or vessels used to store toxic liquids as well as containers holding or submersed in liquids.

In one general aspect, this document features a device for centering a medical instrument in a conduit within a patient. The device comprises a framework of a plurality of elongate metal frame members and a covering that is attached to the framework. The covering is a biocompatible membrane or film. The frame members are attached to each other to define a central lumen having an open proximal end and an open distal end. The distal end has a greater diameter than a diameter of the proximal end. The frame members are attached to each other to further define two or more side apertures that are nearer to the proximal end than to the distal end. In various implementations, the plurality of elongate metal frame members may be comprised of nitinol, wherein the device is collapsible to a low-profile configuration adapted for confinement within a delivery sheath, and wherein the device can self-expand to an expanded configuration when the device is not contained within the delivery sheath. The frame members may be attached to each other to further define four or more side apertures that are nearer to the proximal end than to the distal end. The side apertures may be symmetrically positioned about a longitudinal axis of the device. The side apertures may define open fluid flow paths that are not occluded by the covering. In some embodiments, the plurality of elongate metal frame members form a plurality of petals. In particular embodiments, adjacent petals of the plurality of petals overlap each other. The plurality of petals may be hinged to a proximal end collar of the device.

In another general aspect, this document features a system for treating a human patient. The system comprises a self-centering device, a guidewire comprising an elongate metal wire, and a guide catheter with a lumen. The self-centering device comprises, a framework comprised of a plurality of elongate metal frame members and a covering, wherein the covering is attached to the framework and the covering is a biocompatible membrane or film. The frame members are attached to each other to define a central lumen having an open proximal end and an open distal end. The distal end has a greater diameter than a diameter of the proximal end. The frame members are attached to each other to further define two or more side apertures that are nearer to the proximal end than to the distal end. The self-centering device and the guidewire are arranged to be contained within the lumen, wherein the self-centering device is in a low-profile configuration when the self-centering device is contained within the lumen, and wherein the self-centering device can self-expand to an expanded configuration when the self-centering device is not contained within the lumen.

In general, one aspect of this document features a method for treating a human patient. The method comprises providing a medical device system comprising: a self-centering device; a guidewire comprising an elongate metal wire; and a guide catheter with a lumen, wherein the self-centering device and the guidewire are arranged to be contained within the lumen, wherein the self-centering device is in a low-profile configuration when the self-centering device is contained within the lumen, and wherein the self-centering device can self-expand to an expanded configuration when the self-centering device is not contained within the lumen. The self-centering device comprises: a framework comprised of a plurality of elongate metal frame members, wherein the frame members are attached to each other to define a central lumen having an open proximal end and an open distal end, wherein the distal end has a greater diameter than a diameter of the proximal end, and wherein the frame members are attached to each other to further define two or more side apertures that are nearer to the proximal end than to the distal end; and a covering, wherein the covering is attached to the framework and the covering is a biocompatible membrane or film. The method further comprises inserting the guide catheter containing the self-centering device and the guidewire into the patient; directing the guide catheter to a target site within the patient; causing the self-centering device to emerge from a distal end of the guide catheter, wherein the self-centering device reconfigures from the low-profile configuration to the expanded configuration when the self-centering device emerges from the guide catheter; and causing the guidewire to emerge from a distal end of the guide catheter.

In various implementations, the method can be used to treat a stenotic aortic valve of the patient. In addition, the method can be used to treat perivalvular aortic or mitral valve leaks, or a vascular fistula in the patient.

In another general aspect, this document features a device for centering a medical instrument in a conduit within a patient. The device comprises a flared body comprised of two or more polymeric portions. The two or more polymeric portions are coupleable to each other to define a central lumen having an open proximal end and an open distal end. The distal end has a greater diameter than a diameter of the proximal end. The two or more polymeric portions are attached to each other to further define two or more side apertures that are nearer to the proximal end than to the distal end, wherein the side apertures are symmetrically positioned about a longitudinal axis of the device, and wherein the side apertures define open fluid flow paths that are not occluded by the polymeric portion.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides devices and methods for the treatment of heart conditions such as valvular stenosis. For example, this document provides devices and methods by which a guide catheter can align itself with a blood flow stream to thereby help direct a guidewire or other elongate device transmitted from the guide catheter through an orifice of a heart valve.

One of the most challenging steps when performing a TAVR, valvuloplasty, or hemodynamic study on a stenotic valve is to find the valve orifice and pass a guidewire, catheter, or other elongate medical device through the stenotic valve, against the direction of high velocity blood flow. The current practice involves random probing of the stenotic valve with the guide wire until the orifice is penetrated.

Figure 1A:
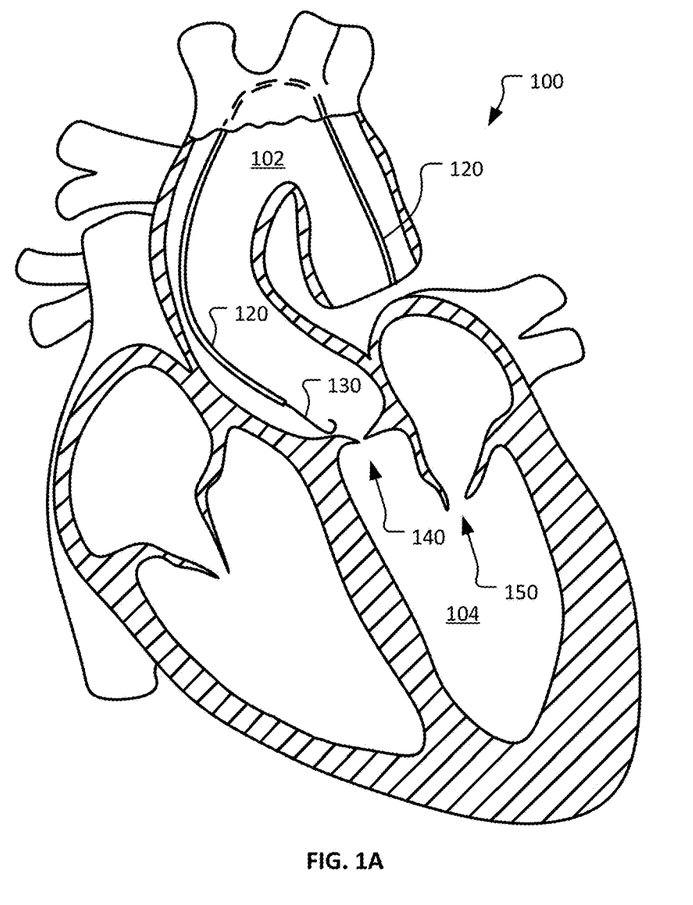
FIG. 1A is a schematic diagram of a human heart shown in partial cross-section undergoing a catheterization using a guide catheter that is intended to transmit a guidewire through an aortic valve orifice.

With reference to FIG. 1, a schematic diagram is provided of human heart 100 shown in partial cross-section undergoing a catheterization using a guide catheter 120. Guide catheter 120 is depicted in aortic arch 102 for the purpose of transmitting a guidewire 130 through the orifice of an aortic valve 140. The blood flow in this region of heart 100 is from a left ventricle 104 to aortic arch 102. Therefore, guide catheter 120 is attempting to insert guidewire against the flow direction of the blood flowing from left ventricle 104 to aortic arch 102.

The process of crossing a heart valve using a guidewire is performed as a step in various heart treatment procedures. For example, TAVR procedures, valvuloplasties, hemodynamic studies on a stenotic valve, and other types of procedures involve the placement of a guidewire through the orifice of a heart valve. In addition to aortic valve procedures, other applications involving the placement of a guidewire through an orifice include perivalvular mitral valve 150 leak treatment procedures (or perivalvular aortic valve leak) and other treatment procedures involving fistulas at any site in the human heart or body.

Aortic valve 140 can be approached by guide catheter 120 via aortic arch 102. In some cases, guide catheter 120 can be percutaneously inserted in a femoral artery of a patient, and directed to the patient's aorta. From the aorta, guide catheter 120 can be directed to aortic arch 102. In other cases, aortic arch 102 can be accessed by guide catheter 120 via the patient's radial artery. Other aortic arch 102 access techniques are also envisioned. While in the depicted embodiment guide catheter 120 is generally linear at its distal end portion, in some embodiments the distal end portion of guide catheter 120 is angled (e.g., a terminal angle). In some embodiments, the terminal angle of guide catheter 120 is in a range of about 0 degrees to about 30 degrees, or about 30 degrees to about 60 degrees, or about 60 degrees to about 90 degrees.

The devices and methods provided herein can be applied to transradial catheterization procedures, transfemoral catheterization procedures, and other aortic arch 102 access techniques. Further, the devices and methods provided herein can also be applied to any type of catheterization procedure that involves a catheter that is directed to a location wherein the catheter is positioned against the flow of a fluid stream, such as a blood stream or other fluid flow stream.

With the distal tip of guide catheter 120 in a position superior to aortic valve 140, guidewire 130 can be ejected from guide catheter 120. The purpose of ejecting guidewire 130 from guide catheter 120 is to insert guidewire 130 through the orifice of aortic valve 140. As depicted in FIG. 1A, the longitudinal axis of guide catheter 120 may not be in alignment with the orifice of aortic valve 140. This can be the case particularly when aortic valve 140 is stenotic. Therefore, as guidewire 130 is ejected from guide catheter 120, the distal tip of guidewire 130 may often contact a leaflet of aortic valve 140 rather than passing through the orifice of aortic valve 140. The current practice for inserting guidewire 130 through aortic valve 140 involves random probing of aortic valve 140 with guidewire 130 until the orifice is penetrated. This practice can be inconvenient and time consuming. This can lead to strokes from dislodgement of calcium and atheroma from the valve leaflets. The devices and methods provided herein simplify and enhance the process of crossing an orifice with guidewire 130.

Figure 1B:
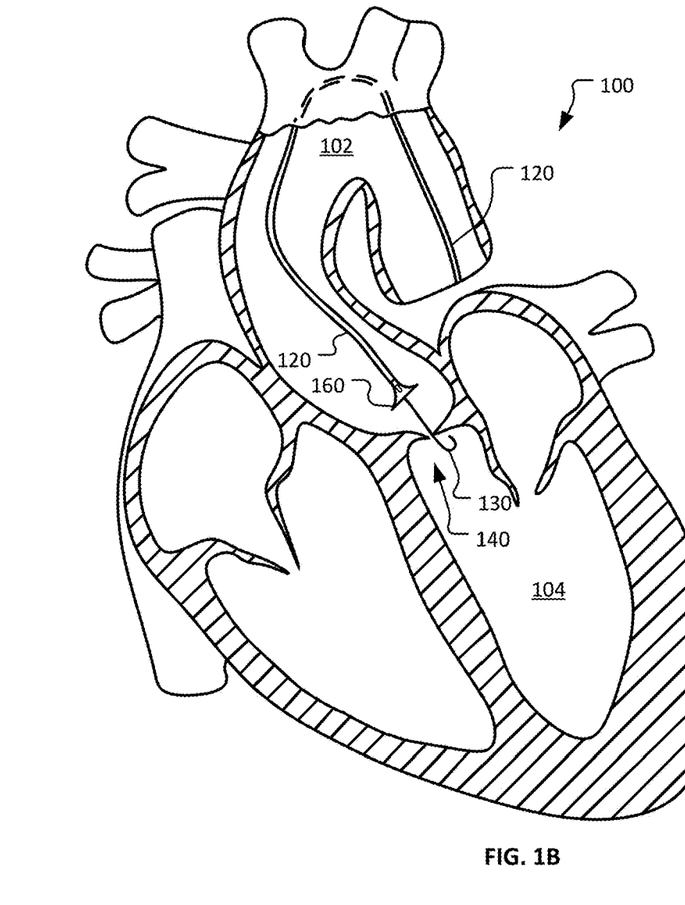
FIG. 1B is a schematic diagram of a human heart shown in partial cross-section undergoing a catheterization using a self-centering guide catheter to transmit a guidewire through an aortic valve orifice in accordance with some embodiments provided herein.

With reference to FIG. 1B, heart 100 is shown in partial cross-section undergoing a catheterization using guide catheter 120. Guide catheter 120 is in aortic arch 102 for the purpose of transmitting guidewire 130 through the orifice of aortic valve 140.

Guide catheter 120 includes a centering device 160. In some embodiments, centering device 160 is collapsible to a low-profile delivery configuration and contained within guide catheter 120 during the insertion of guide catheter 120 into and within the patient as described herein. When the distal tip of guide catheter 120 reaches the target site, such as the position superior to aortic valve 140 as shown, then centering device 160 can be ejected from guide catheter 120. In some embodiments, centering device 160 is self-expanding such that centering device 160 reconfigures itself from the low-profile delivery configuration to an expanded configuration as shown. In the expanded configuration, centering device 160 resembles a bell shape. In some embodiments, guidewire 130 is ejected via guide catheter 120 and generally through the central longitudinal axis of centering device 160.

When centering device 160 is located in a fluid flow path, the shape of centering device 160 causes centering device 160 to center itself on the fluid flow path. As will be described further herein, the bell shape of centering device 160 is configured to receive or catch a jet flow of fluid (e.g., blood flowing through the orifice of aortic valve 140 in this example). When the jet flow of blood flowing from the orifice of aortic valve 140 contacts an interior side surface of centering device 160, the impact force delivered by the jet flow of blood drives centering device 160 laterally so that the jet flow of fluid is caught in or near to the center of centering device 160. Since centering device 160 is located at the distal end of guide catheter 120, when centering device 160 is centered on the fluid flow, guide catheter 120 is also centered on the fluid flow that is coming from the orifice of aortic valve 140. In this manner, centering device 160 causes the longitudinal axis of guide catheter 120 to be in alignment with the orifice of aortic valve 140. Therefore, when guidewire 130 is ejected from guide catheter 120, guidewire 120 will be in alignment with the orifice of aortic valve 130, and guidewire 120 will be able to cross through aortic valve 130 without making substantial contact with the leaflets of aortic valve 140.

Figure 2A:
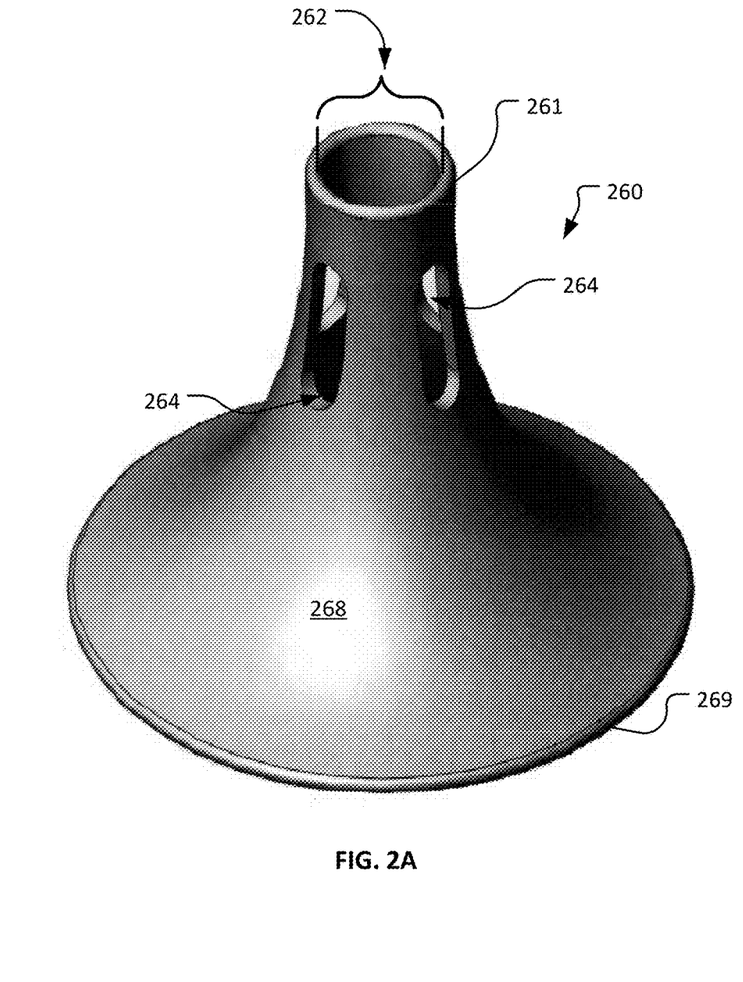
FIGS. 2A and 2B are perspective schematic illustrations of a guide catheter-mounted device for self-centering the guide catheter in accordance with some embodiments provided herein.
Figure 2B:
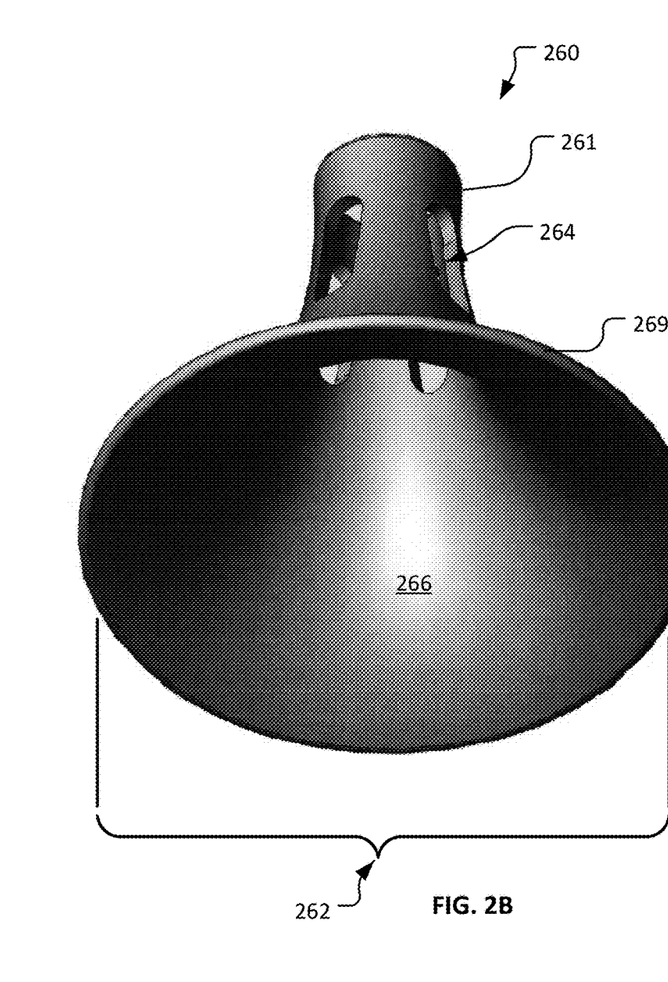

With reference to FIGS. 2A and 2B, a centering device 260 is schematically illustrated in upper and lower perspective viewing angles. These figures illustrate one example embodiment of the general shape and physical features of centering device 260. However, other shapes and physical features are also envisioned. For example, while centering device 260 is illustrated as bell shaped, in some embodiments the centering devices provided herein are cylindrical. In some embodiments, such cylindrically shaped centering devices may have a single central outlet opening.

Centering device 260 includes an inner surface 266 and outer surface 268. Inner and outer surfaces 266 and 268 define an axial lumen 262, apertures 264, a proximal end 261, and a flared distal end 269.

In some embodiments, axial lumen 262 is in alignment with the longitudinal axis of the guide catheter (not shown) that is used to deploy centering device 260. Axial lumen 262 has a greater diameter at flared distal end 269 than at proximal end 261. The diameter of axial lumen 262 gradually decreases from flared distal end 269 to proximal end 261. Axial lumen 262 is configured to transmit a guidewire, catheter, or other elongate device therethrough. Axial lumen 262 is also configured to receive a fluid flow, such as a jet flow of blood from the orifice of a heart valve as described herein. The fluid flow enters axial lumen 262 at flared distal end 269. In that sense, centering device 260 acts like a funnel for catching and collecting fluid flow into axial lumen 262 via flared distal end 269.

A range of multiple different sizes of flared distal end 269 are envisioned, so as to suit different usage variations and body sizes. For example, in some embodiments flared distal end 269 is about 5 to 40 millimeters in diameter, about 10 to 35 millimeters in diameter, about 15 to 30 millimeters in diameter, or about 20 to 25 millimeters in diameter. Other centering device sizes are also contemplated.

Apertures 264 are open areas in the inner and outer surfaces 266 and 268 of centering device 260. In this example embodiment, apertures 264 are located near to proximal end 261 (the end opposite from flared distal end 269). This example embodiment includes four (4) apertures 264. In some embodiments, two, three, five, six, or more than six apertures 264 can be included. Apertures 264 are open areas of centering device 260 that provide a flow path for fluid captured by axial lumen 262 to escape from axial lumen 262. In other words, when centering device 260 is in use, fluid flow can enter into axial lumen 262 at flared distal end 269, and exit out of axial lumen 262 through apertures 264 near proximal end 261.

These proximal apertures help relieve the forces that may tend to push the funnel out of alignment with the jet. In some embodiments, having equally sized apertures positioned in concentric locations also enhances the alignment of the funnel with the high velocity jet, by redirecting the blood flow concentrically in a lateral manner away from the sides of the catheter. In some cases, it may be advantageous to have apertures of different sizes, or apertures nearer the widest part of the funnel.

As fluid flows into axial lumen 262 at flared distal end 269, fluid flow that is out of alignment with the central longitudinal axis of axial lumen 262 (off-center flow) may impact inner surface 266. Such impact may cause centering device 260 to move laterally in response to the impact forces. Such lateral movement will take place so as to balance the lateral impact forces being imparted from the fluid flow to inner surface 266. In other words, centering device 260 will tend to self-center itself with the fluid flowing into axial lumen 262 such that the impact forces imparted by fluid flow are balanced around the central longitudinal axis of axial lumen 262. Hence, when centering device 260 is coupled to a guide catheter 120 (refer to FIG. 1B), centering device 260 can self-center the catheter 120 in relation to a fluid flow, such as a fluid flow through the orifice of aortic valve 140. When catheter 120 is centered in relation to aortic valve 140, guidewire 130 can be ejected from guide catheter 120 and successfully passed through the orifice of aortic valve 140.

In some embodiments, inner surface 266 is parabolic. In some embodiments, inner surface 266 is conical or frusta conical. In some embodiments, inner surface 266 is pyramidal. The angularity of inner surface 266 in relation to the longitudinal axis of axial lumen 262 can range from 0 degrees to 90 degrees.

It should be understood that one or more of the features described in reference to one embodiment can be combined with one or more of the features of any of the other embodiments provided herein. That is, any of the features described herein can be mixed and matched to create hybrid designs, and such hybrid designs are within the scope of this disclosure.

Figure 3A:
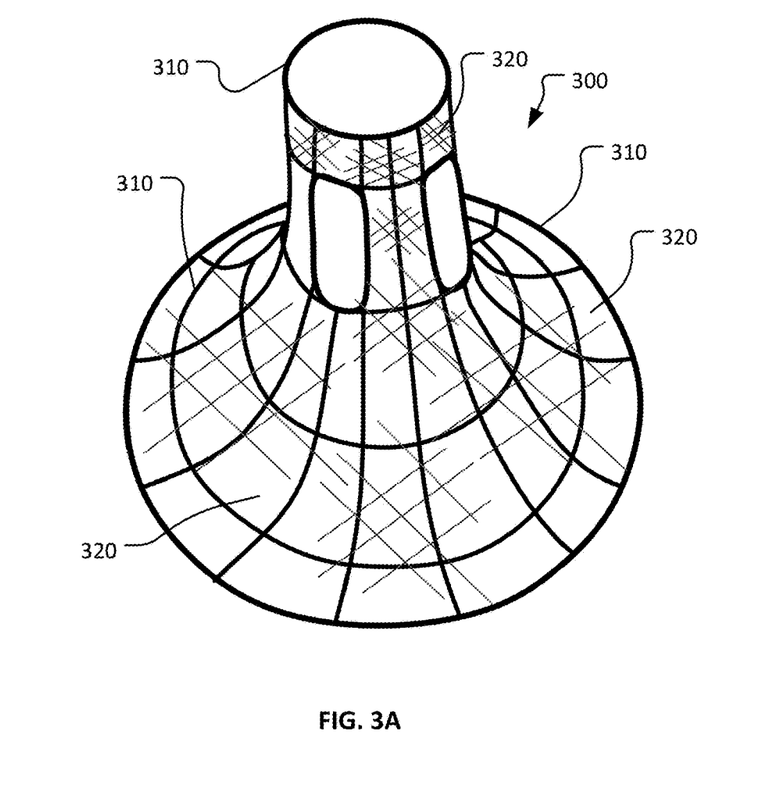
FIG. 3A is an example embodiment of a self-expanding guide catheter-mounted device for self-centering the guide catheter in accordance with some embodiments provided herein.
Figure 3B:
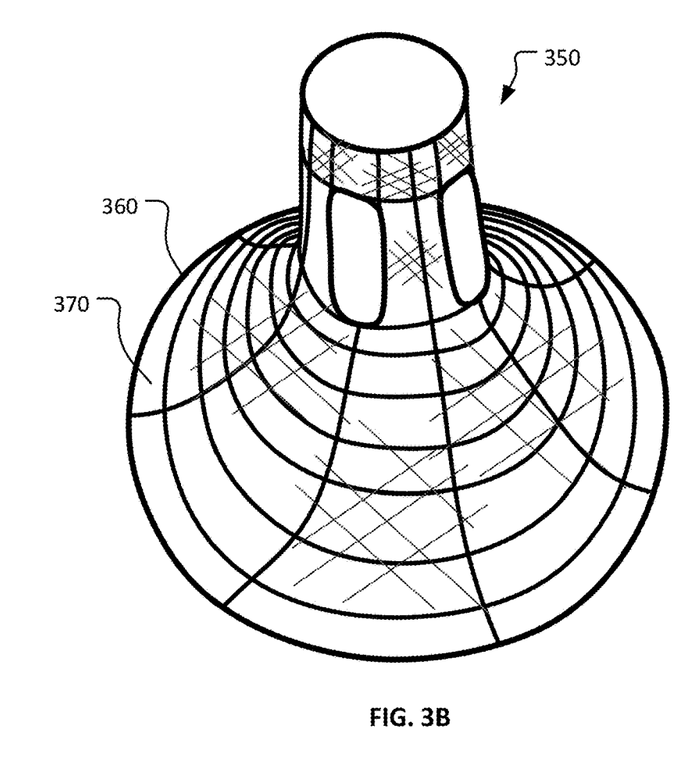
FIG. 3B is another example embodiment of a self-expanding guide catheter-mounted device for self-centering the guide catheter in accordance with some embodiments provided herein.

With reference to FIGS. 3A and 3B, example centering devices 300 and 350 are depicted so as to illustrate some example manners of constructing the catheter-based centering devices provided herein. In the depicted embodiment, centering device 300 is constructed from a plurality of frame members 310 and a covering 320. Similarly, centering device 350 is constructed from a plurality of frame members 360 and a covering 370. Centering device 300 has a majority of frame members 310 configured in a longitudinal direction. In contrast, centering device 350 has a majority of frame members 360 configured in a circumferential pattern (or spiral pattern).

While center devices 300 and 350 are constructed of frame members on which a covering is disposed, in other embodiments catheter-based centering devices can be constructed using other techniques. For example, some catheter-based centering device embodiments are constructed of one or more inflatable members (e.g., balloons). The one or more inflatable members can be attached to a catheter having a lumen through which an inflation medium can pass. In some implementations, the inflation medium is saline. The inflation medium can be supplied to the one or more inflatable members to cause expansion of the one or more inflatable members. Once expanded, the one or more inflatable members can have a bell shape, for example, like that of other catheter-based centering devices provided herein.

Still referring to FIGS. 3A and 3B, frame members 310 and 360 are a compilation of elongate structural members that are attached together to form a framework that creates the bell-shape of centering devices 300 and 350. Frame members 310 and 360 can be metallic, for example, constructed of nitinol, stainless steel, titanium, or a combination of materials. Frame members 310 and 360 can be wires that are wound and attached together (e.g., welded or glued) to create the bell-shape configuration. Alternatively, frame members 310 and 360 can originally be a tube that is laser cut and expanded into to the desired bell-shape configuration, and heat-set to make the bell-shape the natural configuration of frame members 310 and 360. In some embodiments, frame members 310 and 360 can have a polymeric covering or powder coating over or on the metallic frame members 310 and 360.

In general, frame members 310 and 360 can be collapsible to fit within the lumen of a catheter. Frame members 310 and 360 can radially self-expand to the bell-shaped unconstrained configuration as shown when deployed from the catheter. Self-expanding frame members 310 and 360 are often comprised of super elastic shape-memory nitinol (NiTi) material. In some embodiments, a secondary device such as a balloon is used to provide a temporary supplemental radial force to help expand frame members 310 and 360 into the bell-shape shown. Frame members 310 and 360 may be alternatively comprised of stainless steel or other materials. Frame members 310 and 360 can be fabricated in various manners, such as by forming a wire, or by laser cutting a tube, and the like. In some embodiments, frame members 310 and 360 can be heat-set in a desired shape, such as the bell-shape. These and all other variations of frame member types, material compositions, material treatments, configurations, fabrication techniques, and methods for attaching coverings to frame members 310 and 360 are envisioned and within the scope of the centering devices provided herein.

In some embodiments, the entire bell shaped segment is constructed entirely out of a polymer that can be collapsed into a tubular structure for delivery via the guide catheter, following which it can spring open to form a bell shaped funnel with side apertures. In some such embodiments, the polymeric bell shaped structure includes pleats and/or living hinges that facilitate the collapsibility and expandability of the device.

In some embodiments, a bell shaped centering device (e.g., a funnel shape) is constructed of two, three, four, five, six, or more than six petal shaped segments that can collapse for containment within a delivery sheath or guide catheter. Upon emergence from the delivery sheath or guide catheter, the petal shaped segments can open up to create a funnel shape (e.g., in a manner like the blooming of a flower). In some embodiments, the petal shaped segments overlap with each other, particularly when the structure is collapsed and to a lesser extent when the structure is expanded. In some embodiments, the petals are hinged to a central collar. In some embodiments, the petals are constructed of a superelastic material (e.g., nitinol) that facilitates the collapsibility and expandability of the petals. In some embodiments, one or more of the petals includes apertures (e.g., like apertures 264 described above). In some embodiments, the petals are constructed of a framework of elongate elements (e.g., struts or wires made or nitinol or stainless steel) and a covering material is disposed on the framework. In some embodiments, the covering material can be ePTFE and the like.

In some embodiments, frame members 310 and 360 include one or more visualization markers, such as radiopaque markers, bands, or radiopaque filler materials. The radiopaque markers can assist a clinician with in situ radiographic visualization of centering device 310 and 360 so that the clinician can orient the device as desired in relation to the anatomy of the patient.

Centering devices 300 and 350 also includes coverings 320 and 370 respectively. Coverings 320 and 350 may be made of any flexible, biocompatible material capable of acting as a barrier to fluid jet flow, such as that from the orifice of a heart valve. Such materials can include, but are not limited to, Dacron, polyester fabrics, Teflon-based materials, Polytetrafluoroethylene (PTFE), expanded Polytetrafluoroethylene (ePTFE), polyurethanes, metallic film or foil materials, or combinations of the foregoing materials.

Coverings 320 and 350 can be attached to frame members 310 and 360 in a variety of suitable manners well known to those of ordinary skill in the art. For example, in some embodiments, coverings 320 and 350 are sewn to frame members 310 and 360. In some embodiments, coverings 320 and 350 are glued to frame members 310 and 360. In some embodiments, frame members 310 and 360 are sandwiched between layers of coverings 320 and 350. In some embodiments, a combination of such attachment methods are used.

It should be understood that one or more of the features described in reference to one embodiment can be combined with one or more of the features of any of the other embodiments provided herein. That is, any of the features described herein can be mixed and matched to create hybrid designs, and such hybrid designs are within the scope of this disclosure.

Figure 4:
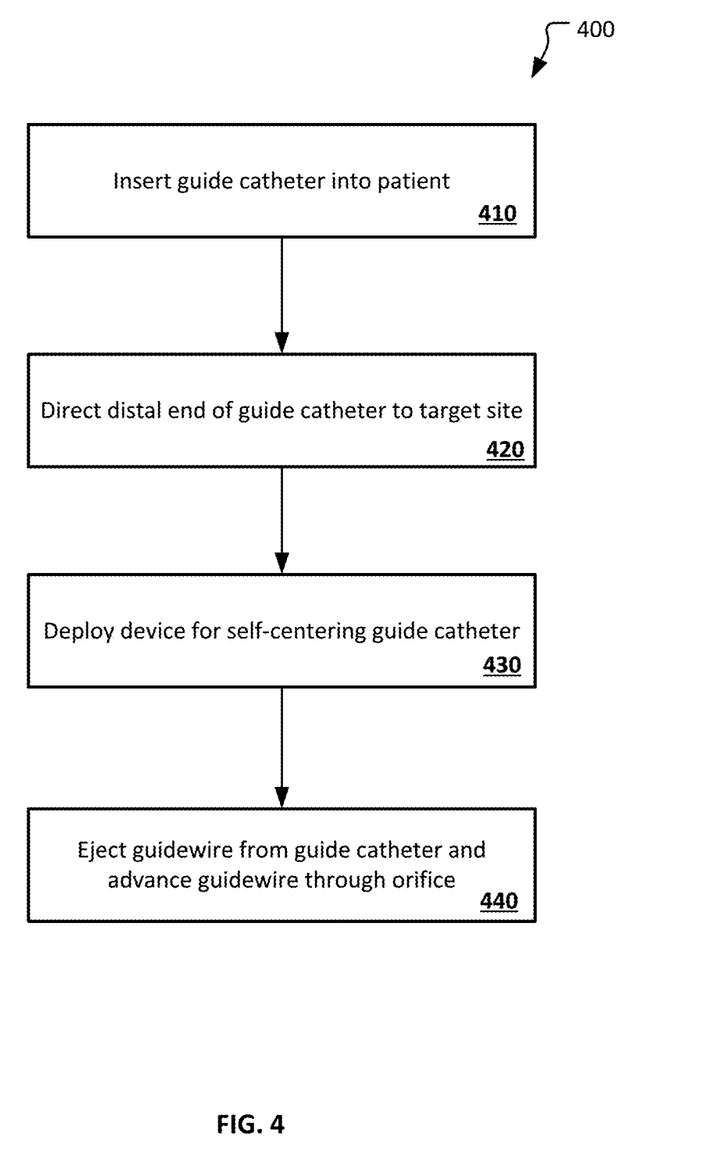
FIG. 4 is flowchart of a heart valve catheterization process in accordance with some embodiments provided herein.

With reference to FIG. 4, an example process 400 for using the devices and systems provided herein is illustrated by a flowchart. In general, process 400 is a method of advancing a guidewire from a catheter through an orifice (such as a heart valve) where a fluid is flowing in a counter direction to the direction the guidewire is being advanced.

At operation 410, a guide catheter is inserted into a patient by a clinician. In some cases, the insertion may be percutaneous. In some cases, the insertion may be through a natural body orifice or channel. The guide catheter can include a guidewire and a self-expanding centering device contained within a lumen of the catheter. The self-expanding centering device (such as wire-framed centering device embodiments 300 and 350 described in reference to FIGS. 3A and 3B) can be in a low-profile collapsed configuration within the lumen of the catheter.

At operation 420, the distal end of the guide catheter is directed to the target site within the body of the patient. Visualization systems such as x-ray fluoroscopy, MRI, or ultrasound can be utilized to assist the clinician with directing the guide catheter within the patient as desired.

At operation 430, when the distal end of the guide catheter is located at the desired site within the patient's body, the clinician can deploy the centering device from the distal end of the guide catheter. As the centering device emerges from the confines of the guide catheter lumen, the centering device can self-expand to the bell-shape as described herein. With the centering device connected to the guide catheter and in the flow path of a fluid (such as blood flow from an orifice of a heart valve), the centering device will receive at least a portion of the fluid that is flowing toward the distal tip of the guide catheter. As described herein, the impact of the fluid on the inner surface of the centering device will cause the centering device to move laterally so as to center itself on the fluid flow. When the fluid flow is from an orifice, the lateral movement of the centering device will cause the centering device (and hence the axis of the guide catheter) to be centered in relation to the orifice.

With the axis of the guide catheter centered on the orifice, the clinician can eject the guidewire from the guide catheter at operation 440. The guidewire will emerge from the guide catheter and be in alignment with the orifice. As such, the guidewire can be advanced through the orifice by the clinician.

Figure 5A:
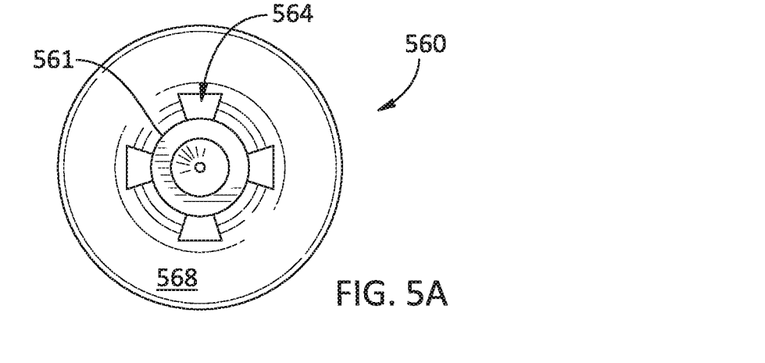
FIG. 5A is a top view of another guide catheter-mounted device for self-centering a guide catheter in accordance with some embodiments provided herein.
Figure 5B:
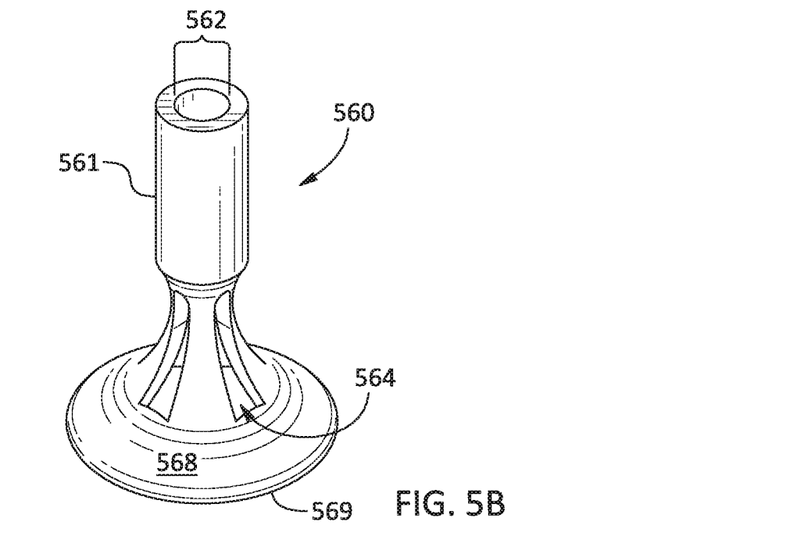
FIG. 5B is a perspective side view of the device of FIG. 5A.
Figure 5C:
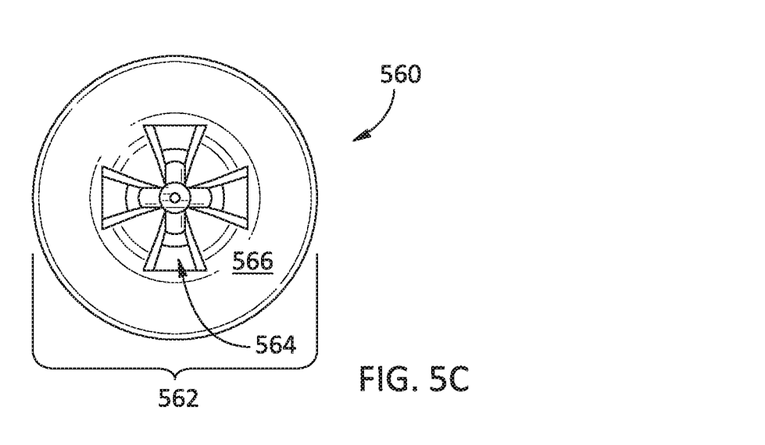
FIG. 5C is a bottom view of the device of FIG. 5A.

With reference to FIGS. 5A, 5B, and 5C a centering device 560 is schematically illustrated in top, side perspective, and bottom viewing angles respectively. These figures illustrate one example embodiment of the general shape and physical features of centering device 560. However, other shapes and physical features are also envisioned. For example, while centering device 560 is illustrated as bell shaped, in some embodiments the centering devices provided herein are cylindrical. In some embodiments, such cylindrically shaped centering devices may have a single central outlet opening.

Centering device 560 includes an inner surface 566 and outer surface 568. Centering device 560 also includes an axial lumen 562, apertures 564, a proximal end collar 561, and a flared distal end 569.

In some embodiments, axial lumen 562 is in alignment with the longitudinal axis of the guide catheter (not shown) that is used to deploy centering device 560. Axial lumen 562 has a greater diameter at flared distal end 569 than at proximal end collar 561. The diameter of axial lumen 562 gradually decreases from flared distal end 569 to proximal end collar 561. Axial lumen 562 is configured to transmit a guidewire, catheter, or other elongate device therethrough.

Axial lumen 562 is also configured to receive a fluid flow, such as a jet flow of blood from the orifice of a heart valve as described herein. The fluid flow enters axial lumen 562 at flared distal end 569. In that sense, centering device 560 acts like a funnel for catching and collecting fluid flow into axial lumen 562 via flared distal end 569.

A range of multiple different sizes of flared distal end 569 are envisioned, so as to suit different usage variations and body sizes. For example, in some embodiments flared distal end 569 is about 5 to 40 millimeters in diameter, about 10 to 35 millimeters in diameter, about 15 to 30 millimeters in diameter, or about 20 to 25 millimeters in diameter. Other centering device sizes are also contemplated.

Apertures 564 are open areas in the inner and outer surfaces 566 and 568 of centering device 560. In this example embodiment, apertures 564 are located along flared distal end 569. This example embodiment includes four (4) apertures 564. In some embodiments, two, three, five, six, or more than six apertures 564 can be included. Apertures 564 are open areas of centering device 560 that provide a flow path for fluid captured by axial lumen 562 to escape from axial lumen 562. In other words, when centering device 560 is in use, fluid flow can enter into axial lumen 562 at flared distal end 569, and exit out of axial lumen 562 through apertures 564 along flared distal end 569.

These proximal apertures help relieve the forces that may tend to push the funnel out of alignment with the jet. In some embodiments, having equally sized apertures positioned in concentric locations also enhances the alignment of the funnel with the high velocity jet, by redirecting the blood flow concentrically in a lateral manner away from the sides of the catheter. In some cases, it may be advantageous to have apertures of different sizes, or apertures nearer the widest part of the funnel.

As fluid flows into axial lumen 562 at flared distal end 569, fluid flow that is out of alignment with the central longitudinal axis of axial lumen 562 (off-center flow) may impact inner surface 566. Such impact may cause centering device 560 to move laterally in response to the impact forces. Such lateral movement will take place so as to balance the lateral impact forces being imparted from the fluid flow to inner surface 566. In other words, centering device 560 will tend to self-center itself with the fluid flowing into axial lumen 562 such that the impact forces imparted by fluid flow are balanced around the central longitudinal axis of axial lumen 562. Hence, when centering device 560 is coupled to a guide catheter 120 (refer to FIG. 1B), centering device 560 can self-center the catheter 120 in relation to a fluid flow, such as a fluid flow through the orifice of aortic valve 140. When catheter 120 is centered in relation to aortic valve 140, guidewire 130 can be ejected from guide catheter 120 and successfully passed through the orifice of aortic valve 140.

In some embodiments, inner surface 566 is parabolic. In some embodiments, inner surface 566 is conical or frusta conical. In some embodiments, inner surface 566 is pyramidal. The angularity of inner surface 566 in relation to the longitudinal axis of axial lumen 262 can range from 0 degrees to 90 degrees.

It should be understood that one or more of the features described in reference to one embodiment can be combined with one or more of the features of any of the other embodiments provided herein. That is, any of the features described herein can be mixed and matched to create hybrid designs, and such hybrid designs are within the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

Non-medical applications of the devices and techniques provided herein are also envisioned. For example, in situations such as leakage of a liquid from an underwater pressure vessel or a pipe conveying liquid or gaseous materials, a self-centering device can be used to hold a tube in place in alignment with the fluid flow jet, following which a suitable device can be passed across the opening or defect in the pipe, container, shipping vessel, and the like.

What is claimed is:

1. A device for self-centering a medical instrument in a conduit within a patient, said device comprising:
    a flared body defining a central lumen, said flared body having a proximal end with a proximal diameter, a flared distal end with a distal diameter greater than the proximal diameter, and an interior side surface extending between said proximal end and said distal end and blocking fluid flow therethrough;
    wherein two or more apertures are defined in said flared body to provide open fluid flow paths through which fluid can pass through said flared body.

2. The device of claim 1, wherein said flared body self-centers with respect to an orifice within the patient as a result of fluid flow through the orifice impacting said interior side surface and driving said flared body laterally to catch the fluid flow in or near to the center of said self-centering device.

3. The device of claim 1, wherein said apertures are configured to redirect fluid flowing in said central lumen laterally away from said flared body.

4. The device of claim 1, wherein the apertures are symmetrically positioned about the central lumen.

5. The device of claim 1, wherein the apertures are equally sized apertures positioned in concentric locations about the central lumen.

6. The device of claim 1, wherein the apertures are nearer to the proximal end than to the flared distal end.

7. A system for centering a medical instrument in a conduit within a patient in relation to a fluid flow path through an orifice within the patient, said system comprising:
a guide catheter with a lumen;
self-centering device having a body shaped to cause said self-centering device to self-center itself on the fluid flow path, said body having an interior side surface contacted by the fluid flow; and
a guidewire;
wherein:
said self-centering device and said guidewire are arranged to be contained within said guide catheter lumen with said self-centering device in a low-profile configuration for delivery to a treatment site; and
said self-centering device self-centers itself as a result of fluid flow impacting said interior side surface.

8. The system of claim 7, wherein:
said body is flared and defines a central lumen, said flared body having a proximal end with a proximal diameter, a flared distal end with a distal diameter greater than the proximal diameter, and an interior side surface extending between said proximal end and said distal end; and
said body expands into an expanded configuration with the distal diameter greater than the proximal diameter when positioned outside said guide catheter.

9. The system of claim 7, wherein said body self-expands upon exiting said guide catheter lumen to reconfigure itself from a low-profile delivery configuration to an expanded configuration.

10. The system of claim 7, wherein said self-centering device is configured to be positioned in a site larger than the conduit so that said self-centering device can move laterally within the conduit to align with the orifice.

11. The system of claim 7, wherein self-centering of said body on the fluid path aligns said body with the orifice in the patient and causes said guide catheter to be aligned with the orifice in the patient, such that when said guidewire is ejected from said guide catheter, said guidewire is aligned with the orifice in the patient and can cross through the orifice without making substantial contact with the orifice walls.

12. The system of claim 7, wherein said self-centering device has an axial lumen extending therethrough, and self-centering device self-centers said catheter in relation to the fluid flowing into said axial lumen such that impact forces imparted by the fluid flow are balanced around a central longitudinal axis of said axial lumen.

13. The system of claim 7, wherein fluid is blocked from flowing through said interior side surface of said self-centering device body.

14. A device for self-centering a medical instrument in a conduit within a patient in relation to a fluid flow through an orifice within the patient, said self-centering device comprising:
a body shaped to cause said self-centering device to center itself on a fluid flow path through the orifice;
wherein the impact force delivered by the fluid flow to said body drives said self-centering device laterally so that the fluid flow is caught in or near to the center of said self-centering device to cause said self-centering device to self-center itself in relation to the fluid flow.

15. The self-centering device of claim 14, wherein said body has an interior side surface contacted by the fluid flow, wherein the impact force delivered by the fluid flow impacts said interior side surface of said body to drive said self-centering device laterally within the conduit.

16. The self-centering device of claim 15, wherein said interior side surface blocks fluid flow therethrough.

17. The self-centering device of claim 14, wherein said body has a proximal end with a proximal diameter, a flared distal end with a distal diameter greater than the proximal diameter, and an axial lumen configured to receive the fluid flow, said centering device acting like a funnel for catching and collecting fluid flow into said axial lumen via said flared distal end of said body to self-center said body within the conduit in relation to the fluid flow through the orifice.

18. The self-centering device of claim 14, wherein the orifice is smaller than the conduit, and said body is sized to move laterally within the conduit to self-center itself in relation to the orifice.

19. The self-centering device of claim 14, wherein said body has a proximal end with a proximal diameter, and a flared distal end with a distal diameter greater than the proximal diameter, said interior side surface extending between said proximal end and said flared distal end.

* * * * *